(12) United States Patent
Boppart et al.

(10) Patent No.: US 10,258,238 B2
(45) Date of Patent: Apr. 16, 2019

(54) METHOD AND APPARATUS FOR OCT-BASED VISCOMETRY

(71) Applicant: The Board of Trustees of the University of Illinois, Urbana, IL (US)

(72) Inventors: Stephen A. Boppart, Champaign, IL (US); Guillermo Luciano Monroy, Burbank, IL (US); Paritosh Pande, Richland, WA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/880,734

(22) Filed: Jan. 26, 2018

(65) Prior Publication Data

US 2018/0242847 A1 Aug. 30, 2018

Related U.S. Application Data

(60) Provisional application No. 62/460,399, filed on Feb. 17, 2017.

(51) Int. Cl.
*G01B 9/02* (2006.01)
*A61B 5/00* (2006.01)
(Continued)

(52) U.S. Cl.
CPC ............ *A61B 5/0066* (2013.01); *A61B 1/227* (2013.01); *A61B 5/7257* (2013.01); *G01N 11/00* (2013.01);
(Continued)

(58) Field of Classification Search
CPC ..... A61B 3/102; A61B 5/0066; A61B 5/7257; A61B 5/0073; A61B 5/0075; A61B 1/227;
(Continued)

(56) References Cited

U.S. PATENT DOCUMENTS 7,586,618 B2  9/2009  Marks et al.
7,623,908 B2  11/2009  Boppart et al.
(Continued)

FOREIGN PATENT DOCUMENTS

WO   WO 02/088705 A2   11/2002

OTHER PUBLICATIONS

Hiss et al, Diffusion in High Viscosity Liquids, AIChE Journal, vol. 19, No. 4, pp. 698-703.*
(Continued)

*Primary Examiner* — Tarifur R Chowdhury
*Assistant Examiner* — Jonathon Cook
(74) *Attorney, Agent, or Firm* — Sunstein Kann Murphy & Timbers LLP

(57) ABSTRACT

Methods and apparatus for ascertaining a relative viscosity characterizing a fluid sample. The fluid sample is illuminated through a scattering membrane adjacent to the fluid with broadband radiation. Scattering from particles within the fluid sample characterized by a distribution of characteristic dimensions spanning at least two orders of magnitude is detected, generating a detector signal as a function of depth relative to a specified surface of the scattering membrane at a plurality of temporal delays. A cross-correlation function of at least one of amplitude, phase and intensity of a scattered optical field is derived for a plurality of depths relative to the specified surface. A mean cross-correlation function is then derived for each depth and fit to obtain a diffusion coefficient, from which a relative viscosity characterizing the fluid is derived.

6 Claims, 8 Drawing Sheets
(8 of 8 Drawing Sheet(s) Filed in Color)

(51) Int. Cl.
*A61B 1/227* (2006.01)
*G01N 11/00* (2006.01)
*G01N 21/47* (2006.01)
*A61B 6/00* (2006.01)
*A61B 6/03* (2006.01)

(52) U.S. Cl.
CPC ........ *G01N 21/4795* (2013.01); *A61B 5/0075* (2013.01); *A61B 6/032* (2013.01); *A61B 6/508* (2013.01); *A61B 2503/40* (2013.01); *G01B 9/02044* (2013.01); *G01B 9/02091* (2013.01)

(58) Field of Classification Search
CPC ..... A61B 6/508; A61B 6/032; A61B 2503/40; G01B 9/02044; G01B 9/02091; G01B 9/0209; G01N 21/4795; G01N 11/00; G01N 11/006
USPC .................................................. 356/479, 497
See application file for complete search history.

(56) References Cited

U.S. PATENT DOCUMENTS

| | | | |
|---|---|---|---|
| 7,725,169 | B2 | 5/2010 | Boppart et al. |
| 7,787,129 | B2 | 8/2010 | Zysk et al. |
| 8,115,934 | B2 | 2/2012 | Boppart et al. |
| 2003/0082104 | A1 | 5/2003 | Mertelmeier |
| 2004/0181128 | A1 | 9/2004 | Masters |
| 2006/0276709 | A1 | 12/2006 | Khamene et al. |
| 2009/0185191 | A1 | 7/2009 | Boppart et al. |
| 2010/0094137 | A1 | 4/2010 | Furlong et al. |
| 2013/0060131 | A1 | 3/2013 | Oghalai et al. |
| 2014/0036272 | A1* | 2/2014 | Nadkarni ........... G01N 21/4795 356/450 |
| 2014/0378846 | A1* | 12/2014 | Hosoda ................ A61B 5/6876 600/478 |
| 2015/0351606 | A1 | 12/2015 | Ruppersberg et al. |
| 2016/0007840 | A1 | 1/2016 | Boppart et al. |
| 2017/0160148 | A1* | 6/2017 | Saeki ........................ G01L 1/24 |

OTHER PUBLICATIONS

American Academy of Family Physicians, "Otitis Media With Effusion," *Pediatrics*, vol. 113, No. 5, pp. 1412-1429 (May 2004).
Hall-Stoodley et al., "Direct Detection of Bacterial Biofilms on the Middle-Ear Mucosa of Children with Chronic Otitis Media," *JAMA*, vol. 296, No. 2, pp. 202-211 (Jul. 2006).
Jung et al., "Handheld Optical Coherence Tomography Scanner for Primary Care Diagnostics," *IEEE T Bio-Med. Eng.*, vol. 58, No. 3, pp. 741-744 (Mar. 2011).
Marks et al., "Inverse scattering for frequency-scanned full-field optical coherence tomography," *J. Opt. Soc. Am. A*, vol. 24, No. 4, pp. 1034-1041 (Apr. 2007).
Nguyen et al., "Noninvasive in vivo optical detection of biofilm in the human middle ear," *Proc. Nat. Acad. Sci.*, vol. 109, No. 24, pp. 9529-9534 (Jun. 2012).
Pitris et al., "High-Resolution Imaging of the Middle Ear with Optical Coherence Tomography: A Feasibility Study," *Arch. Otolaryngol.*, vol. 127, pp. 637-642 (Jun. 2001).
Reed et al., "Gradient-index fiber-optic microprobes for minimally invasive in vivo low-coherence interferometry," *Opt. Lett.*, vol. 27, No. 20, pp. 1794-1796 (Oct. 2002).
Shelton et al., "Optical coherence tomography for advanced screening in the primary care office," *J. Biophotonics*, pp. 1-9, (Apr. 2013).
Takata et al., "Evidence Assessment of the Accuracy of Methods of Diagnosing Middle Ear Effusion in Children with Otitis Media with Effusion," *Pediatrics*, vol. 112, No. 6, pp. 1379-1387 (Dec. 2003).
Xi et al., "High-resolution three-dimensional imaging of biofilm development using optical coherence tomography," *J. Biomed. Opt.*, vol. 11, No. 3, pp. 134001-1-134001-6 (May/Jun. 2006).
Zysk et al., "Computational methods of analysis of human breast tumor tissue in optical coherence tomography images," *J. Biomed. Opt.*, vol. 11, No. 5, pp. 054015-1-054015-7 (Sep./Oct. 2006).
HEINE BETA® 200 Fiber Optic Otoscope, 1 page.
Welch Allyn Macro View™ sell sheet, 2 pages (2008).
Monroy et al., "Non-invasive Depth-Resolved Optical Measurements of the Tympanic Membrane and Middle Ear for Differentiating Otitis Media," *The Laryngoscope*, vol. 125, pp. E276-E282 (2015).
Van der Jeught et al., "Full-field thickness distribution of human tympanic membrane obtained with optical coherence tomography," *J. Association for Research in Otolaryngology*, vol. 14, pp. 483-494 (2013).
Monroy, "Non-Invasive Optical Quantification of Otitis Media and Middle Ear Effusions," Master's Thesis, University of Illinois at Urbana-Champaign, 85 pages (2013).
Kalkman et al., "Path length resolved diffusive particle dynamics in spectral domain OCT," *Phys. Rev. Lett.*, vol. 105, 198302 (2010).
Lee et al., "Quantitative Imaging of Cerebral Blood Flow Velocity and Intracellular Motility using Dynamic Light Scattering—Optical Coherence Tomography," *J. Cerebral Blood Flow & Metabolism*, vol. 33, pp. 819-825 (2013).
Lee et al., "Dynamic light scattering optical coherence tomography," *Opt. Exp.*, vol. 20, pp. 22262-22277 (2012).
Kim et al., "Imaging and quantifying Brownian motion of micro- and nanoparticles using phase-resolved Doppler variance optical coherence tomography," *J. Biomed. Opt.*, vol. 18, 030504 (2013).
Secomb et al., "Blood Viscosity in Microvessels: Experiment and Theory," *C R Phys.*, vol. 14, pp. 470-478 (2013).

* cited by examiner

Fig. 1B
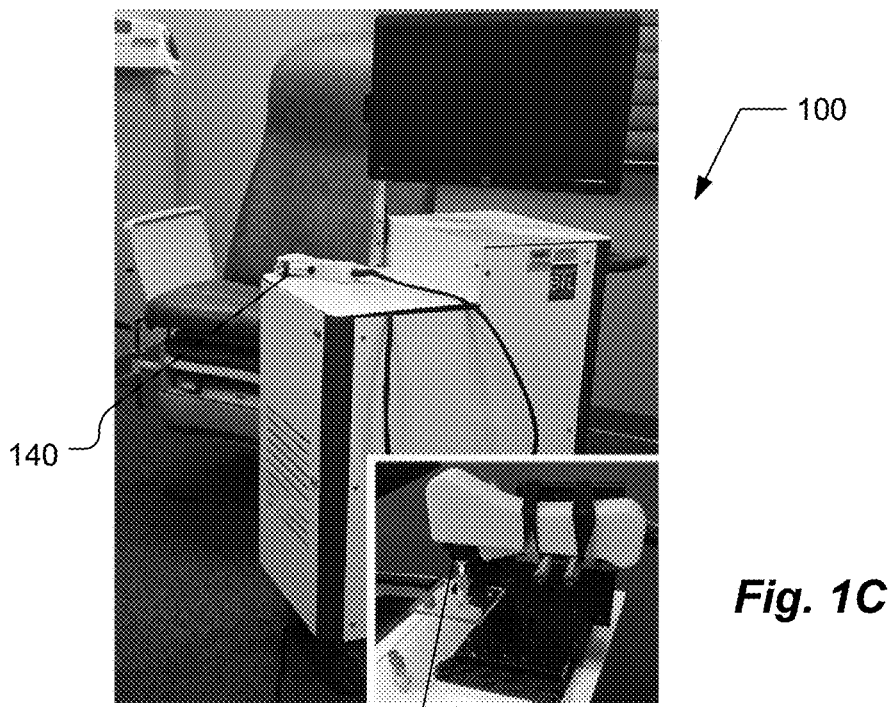
Fig. 1C
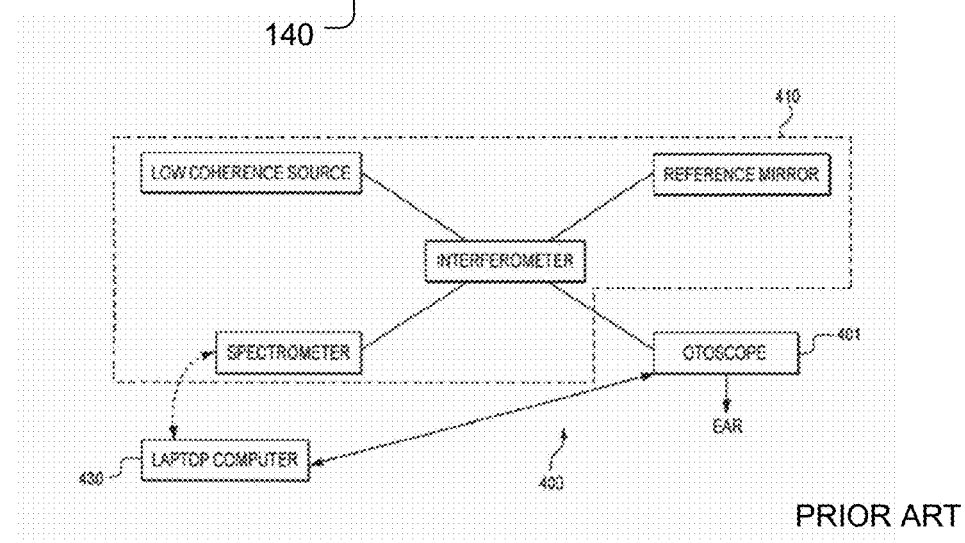
PRIOR ART
Fig. 1D

Fig. 2A
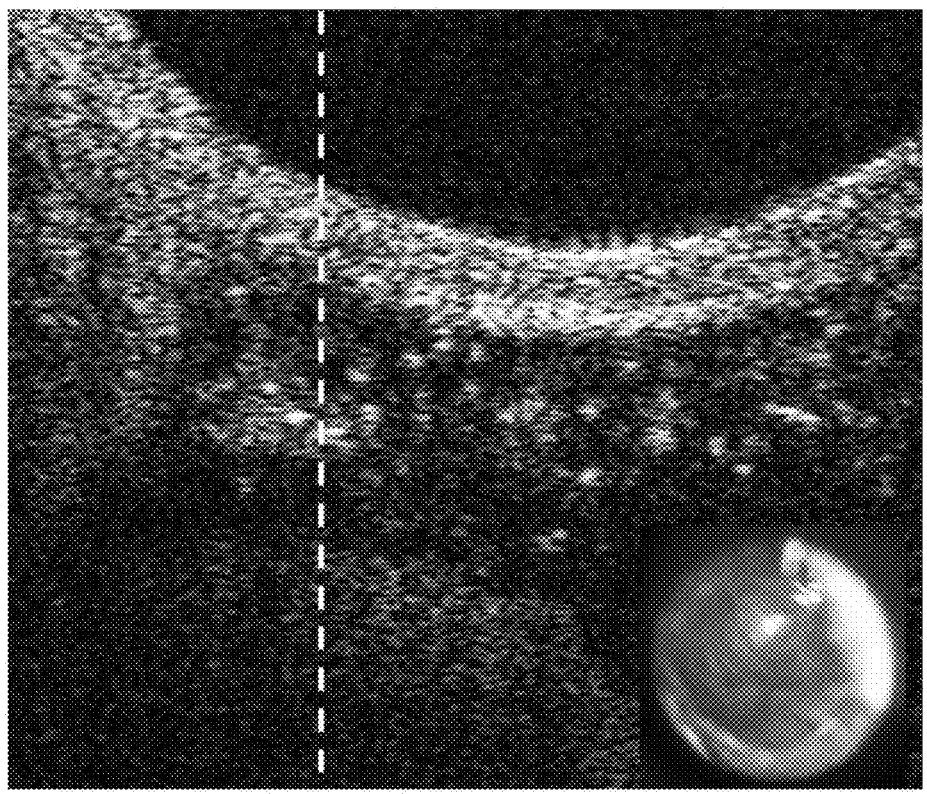
Fig. 2B
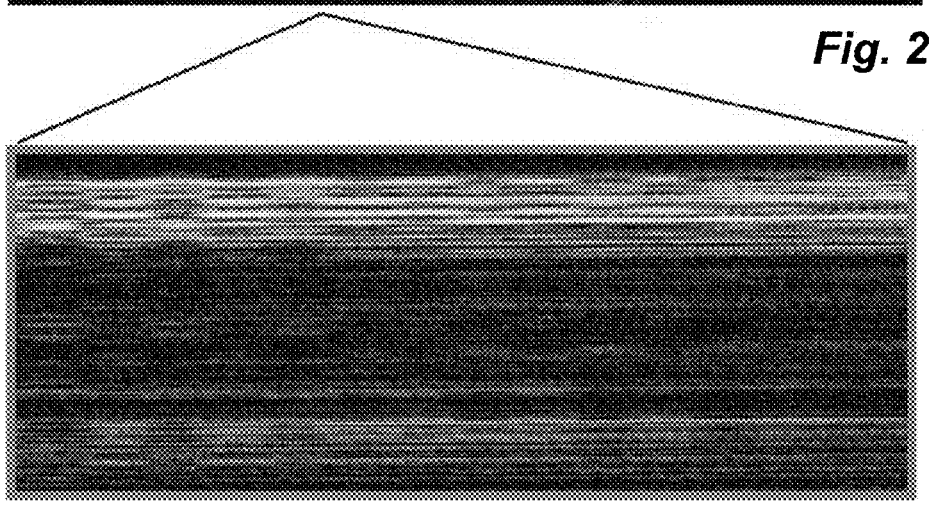
Fig. 2C

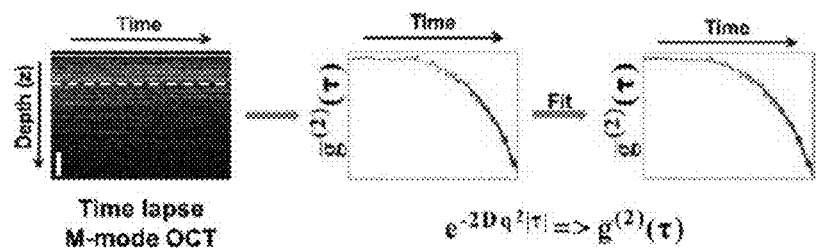
*Fig. 3A*   *Fig. 3B*   *Fig. 3C*

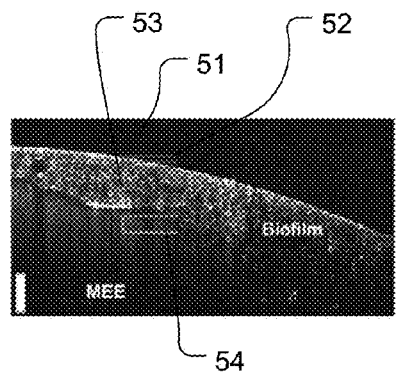 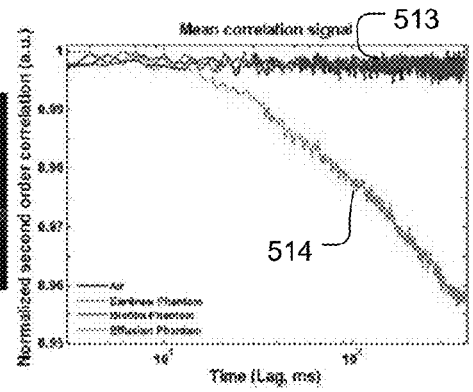
Fig. 5A                    Fig. 5B
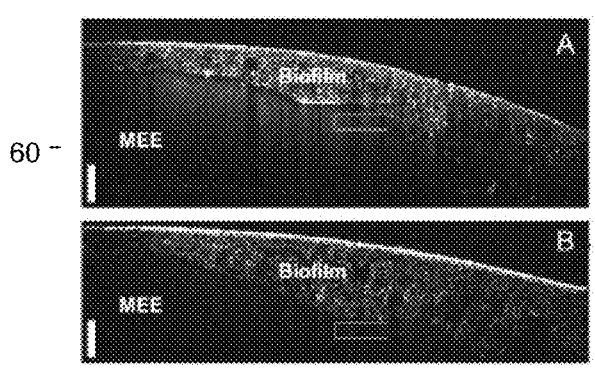 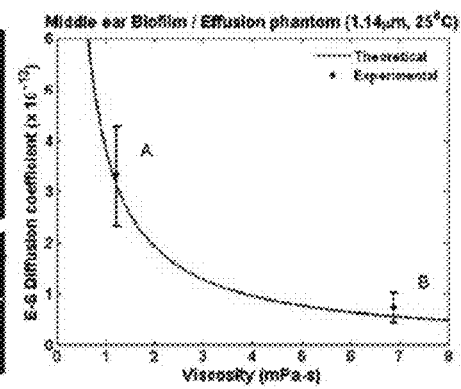
Fig. 6A                    Fig. 6B

Fig. 8A
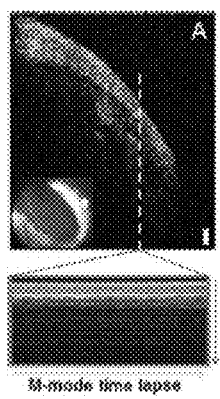
Fig. 8C
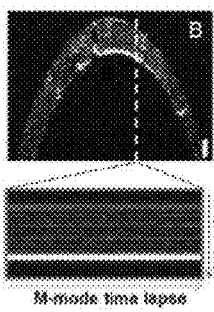
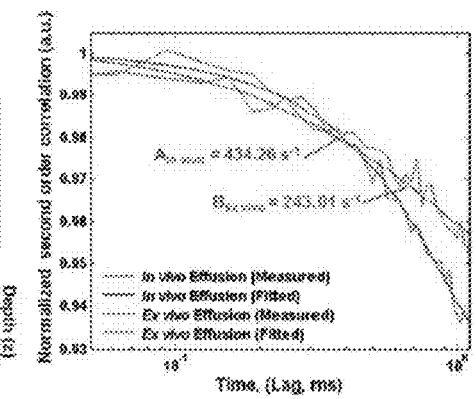
Fig. 8B      Fig. 8D      Fig. 8E

METHOD AND APPARATUS FOR OCT-BASED VISCOMETRY

The present application claims priority of U.S. Provisional Patent Application Ser. No. 62/460,399, filed Feb. 17, 2017 and incorporated herein by reference.

This invention was made with government support under grant R01 EB013723 awarded by the National Institutes of Health. The government has certain rights in the invention.

TECHNICAL FIELD

The present invention relates to apparatus and methods for determining a viscosity of a fluid, and, more particularly, to apparatus and methods for determining a viscosity of a biofilm or middle ear effusions using optical coherence tomography (OCT).

BACKGROUND ART

A middle ear effusion (MEE) is a collection of fluid within the middle ear, and is indicative and characteristic of inflammation in the ear. An effusion commonly results from the blockage, constriction, or dysfunction of the Eustachian tube commonly associated with otitis media (OM), or middle-ear infection. This dysfunction causes negative pressure to develop in the middle ear cavity, which draws out fluid from the surrounding middle ear and mastoid tissue. At least 75% of children under 3 years of age have experienced some form of OM and MEE, as discussed by Ramakrishnan et al., "Diagnosis and treatment of otitis media," Am. Family Physician, vol. 76, pp. 1650-58, (2007), which is incorporated herein by reference. Depending on the infectious conditions of the ear and the immune response of the body, MEEs can become increasingly purulent and mucous-filled. Typically, MEEs can persist for weeks or months, and can eventually lead to the formation of a "glue ear," or a thick, mucoid effusion. The altered viscosity of a MEE prevents efficient clearance by middle-ear cilia, and likely is related to repeated episodes of OM.

It is therefore critical to accurately diagnose and characterize the many different presentations of OM, including MEEs, to ensure that appropriate and sufficient treatment is provided to the patient. Generally, MEEs may be serous or mucoid, can eventually become purulent, and may present a host of other OM related symptoms (e.g. injection, inflammation, or pain). Clinically, MEEs can cause varying degrees of hearing loss in the short term. In the long term, MEEs can cause even more serious complications such as structural damage to finer structures in the middle ear, and speech or learning delays if left untreated. Prescribing an effective treatment for MEEs is difficult, as antibiotics may not immediately clear an effusion, and surgery may be an unnecessary risk if there is not sufficient cause for concern (e.g. hearing loss, speech delay, damage to middle ear bones, persistence for longer than 3-6 months, etc.). However, the persistence and prevalence of OM is the reason why it is one of the most common surgically treated conditions in children under anesthesia.

The presence and the degree of severity of a MEE is not always clear when observed with standard otoscopic methods, which is why pneumatic otoscopy is often cited as the "gold-standard" to assess the presence of MEEs, although rarely performed in practice. Tympanometry and acoustic reflectometry techniques are also useful to help identify MEEs, but are recommended to be compared alongside pneumatic otoscopy results. Tympanocentesis, the removal of a MEE by aspiration through a needle, can be performed to remove and directly examine a MEE, but it is rarely performed in most primary care clinics as it is considered an invasive procedure that carries additional risk to the patient. Ultrasound-based methods lack the spatial resolution to accurately resolve middle ear biofilms, and typically require unobstructed water-based coupling through the outer ear canal. As a result, the method described below, in accordance with the present invention, presents a solution to the unmet need for a technique in the clinician's toolbox that can visually identify and quantitatively characterize a MEE, as well as assess the middle ear for infection noninvasively and in vivo.

The relation of diffusion to viscosity embodied by the Einstein-Stokes equation was first expressed in Einstein's 1905 Brownian motion paper. The use of DLS to derive the diffusion coefficient of particles in a fluid was pioneered by Willis H. Flygare, late professor of chemistry at the University of Illinois, and others, in the early 1970s.

Prior art examples of applying OCT to DLS may be found in Kalkman et al., "Path length resolved diffusive particle dynamics in spectral domain OCT," Phys. Rev. Lett., vol. 105, 198302 (2010), Lee et al., "Dynamic light scattering optical coherence tomography," Opt. Exp., vol. 20, pp. (2012), and in Kim et al., "Imaging and quantifying Brownian motion of micro-and nanoparticles using phase-resolved Doppler variance optical coherence tomography," J. Biomed. Opt., vol. 18, 030504 (2013), all of which are incorporated herein by reference. DLS is a widely applied in many fields, including medicine and biophysics, and is used to determine the Stokes-Einstein (S-E) diffusion coefficient of particles undergoing Brownian motion by analyzing the intensity cross-correlation of the light scattered from the diffusing particles. Since the backscattering cross-section is the primary source of contrast in OCT, DLS measurements can be readily performed using OCT data.

One technique that uses Doppler variance rather than cross-correlation techniques may be found in Kim et al., "Imaging and quantifying Brownian motion of micro-and nanoparticles using phase-resolved Doppler variance optical coherence tomography," J. Biomed. Opt., vol. 18, 030504 (2013), which is incorporated herein by reference. While Doppler variance is a scattering technique like that of the present invention, Doppler variance requires a flowing particle stream, whereas DLS does not.

OCT imaging of the middle ear has been the subject of various Boppart et al. presentations, publications and patents, such as Monroy et al, "Noninvasive depth-resolved optical measurements of the tympanic membrane and middle ear for differentiating otitis media," The Laryngoscope, vol. 125, pp. E276-82. (2015), which is incorporated herein by reference.

Prior to the present invention, however, it was not known that particles in middle ear effusions and in other biofilms may be characterized in a manner that lends itself to OCT measurement of diffusion, and thus to derivation of a viscosity, based on OCT measurement, subject to a calibration. The inventions described herein, furthermore, reflect the recognition of the utility and the clinical application of OCT-based viscosity measurement to diagnosis of middle ear pathologies.

SUMMARY OF EMBODIMENTS OF THE INVENTION

In accordance with embodiments of the invention, methods are provided for A method for ascertaining a relative viscosity characterizing a fluid sample. The method has steps of:

illuminating the fluid sample through a scattering membrane adjacent to the fluid with broadband radiation having a fraction bandwidth, at half-maximum, of at least 10%;

detecting scattering from scattering particles within the fluid sample, the scattering particles characterized by a distribution of characteristic dimensions spanning at least two orders of magnitude;

generating a detector signal as a function of depth relative to a specified surface of the scattering membrane at a plurality of temporal delays;

interferometrically deriving at least one of amplitude, phase and intensity of a scattered field for a plurality of depths relative to the specified surface;

calculating a mean cross-correlation function for each depth;

fitting the mean cross-correlation function for the plurality of depths to obtain a diffusion coefficient; and deriving the relative viscosity characterizing the fluid based on the diffusion coefficient.

In accordance with other embodiments of the present invention, illuminating the fluid sample through a scattering membrane adjacent to the fluid may include transmitting the broadband radiation through an intervening biological membrane. The intervening biological tissue may be a tympanic membrane and the fluid sample may be a middle ear effusion.

In further embodiments, a decay rate of cross-correlations taken between successive time-dependent cross-correlation functions from the interferometer may be calibrated relative to viscosity on the basis of a reference fluid of known viscosity.

In yet further embodiments of the present invention, a middle ear effusion may be graded with respect to at least one of serosity and mucosity on the basis of relative viscosity.

BRIEF DESCRIPTION OF THE DRAWINGS

The current patent or application file contains at least one drawing executed in color. Copies of this patent or patent application publication with color drawing(s) will be provided by the Office upon request and payment of the necessary fee.

The foregoing features of the invention will be more readily understood by reference to the following detailed description, taken with reference to the accompanying drawings, in which:

FIG. 1B shows the handheld OCT system that may be used in practicing embodiments of the present invention. FIG. 1C shows a handheld probe in a mounted configuration used to measure phantom samples or aspirated ex vivo middle ear effusions. FIG. 1D schematically depicts salient components of a prior art OCT imaging system.

FIG. 2A shows an in vivo Optical Coherence Tomography (OCT) image of a human tympanic membrane (TM) and Middle Ear Effusion (MEE), while inset FIG. 2B is a CCD image of the TM surface. FIG. 2C shows M-mode time-lapse data taken repeatedly at the white dotted line (of FIG. 2A) through time.

FIGS. 3A-3C depict how a S-E diffusion coefficient is calculated for a sample, in accordance with an embodiment of the present invention. FIG. 3A shows resampling of the raw spectral domain M-mode OCT data. FIG. 3B plots a temporal intensity cross-correlation function, and FIG. 3C plots an average of the resulting cross-correlation functions over repeated measurements.

FIG. 5A depicts an OCT-generated image of Middle Ear Effusion. Brackets correspond to the depth ranges analyzed to produce the data displayed in FIG. 5B.

FIG. 6A Stokes-Einstein diffusion coefficient measurements of middle ear phantoms, with calculated S-E diffusion coefficients plotted in FIG. 6B. The phantoms (A, B) each contain a different effusion-like suspension (suspension of water, glycerol, and micro-particle mixtures) to mimic the physiological qualities of a 'serous' and 'mucoid' middle ear effusion. Scale bars represent 100 µm in depth.

FIGS. 8A-8E the comparison between two separate MEE samples. FIG. 8A shows an in vivo cross-sectional OCT image and inset high-resolution otoscope image a thick effusion, while FIG. 8C shows an effusion from another patient. FIGS. 8B and 8D show cross-sectional images of the respective aspirated ex vivo MEEs in an exudate trap, with the subsequently measured time-lapse M-mode OCT data. The plot in FIG. 8E shows the comparison of the normalized second order correlation plots of the aspirated ex vivo MEEs

DETAILED DESCRIPTION OF EMBODIMENTS OF THE INVENTION

Figure 1A:
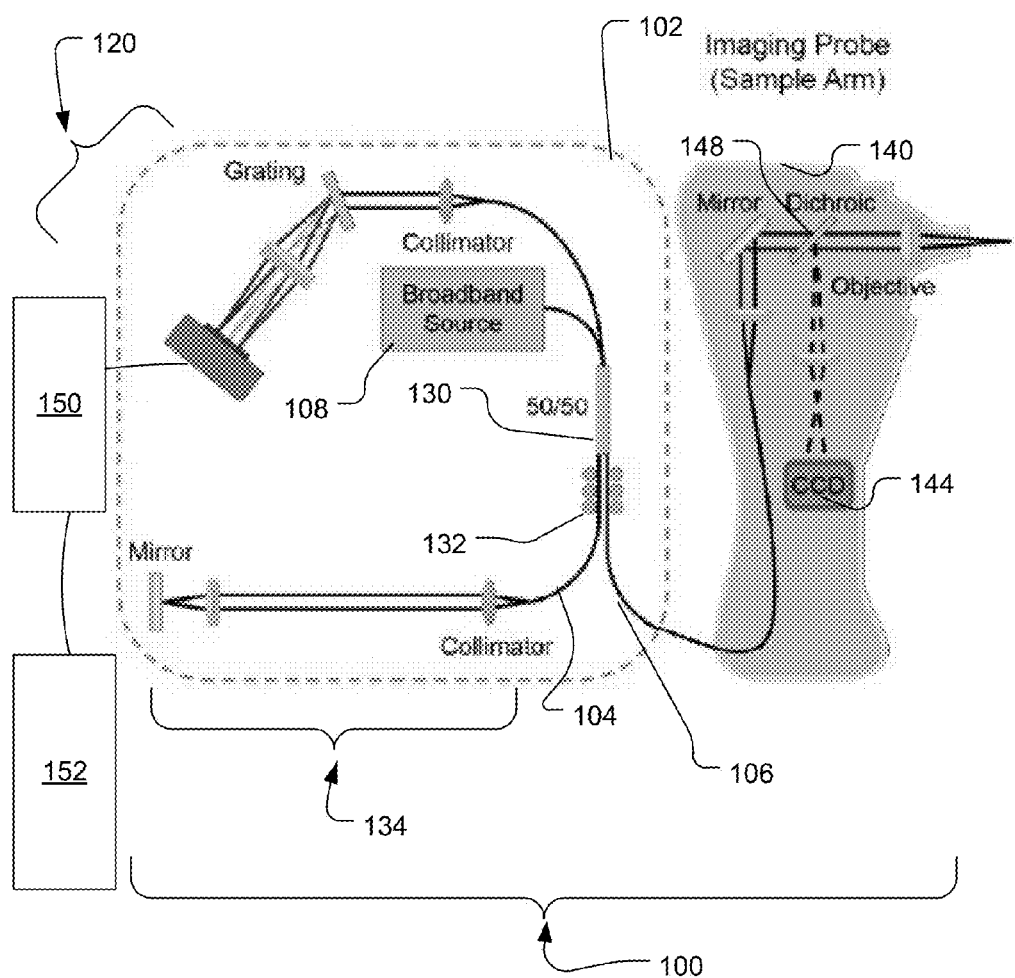
FIG. 1A shows a schematic depiction of a handheld OCT system for measuring fluid viscosity in accordance with an embodiment of the present invention.

Definitions:

The "viscosity" of a fluid (typically measured in poise, or centipoise, where a centipoise is 1 mPa·s) is the resistance of the fluid to shearing flow. Viscosity is denoted herein by the symbol $\eta$.

A "diffusion coefficient," denoted herein by the symbol D, expresses the proportionality of particle flux to concentration gradient.

A "characteristic dimension" of a particle refers to a linear dimension of the order of the distance from the centroid of a particle to the furthest point on its surface.

An "order of magnitude" shall refer to a power of 10.

The term "biological membrane," used herein synonymously with "membrane," is a layer (or multiple layers) of tissue partitioning two structures, where "tissue" is an ensemble of similar cells.

A "biofilm" is defined as a group of bacterial microorganisms within a self-produced extracellular polymer matrix, as may be found affixed to the TM and middle ear mucosa and is commonly found in chronic or recurrent OM.

The relation of viscosity to the diffusion coefficient of a fluid is expressed by the Stokes-Einstein (S-E) equation, which represents the inverse proportionality of viscosity to the diffusivity of a spherical particle of a specified size in a suspension of particles in a fluid of low Reynolds number. See Einstein, "*On the Motion of Small Particles Suspended in Liquids at Rest Required by the Molecular-Kinetic Theory of Heat,*" *Annalen der Physik*, vol. 17, pp. 549-560 (1905).

Thus, if the diffusion coefficient for particles of a specified size, characteristic dimension, or size distribution can be measured using OCT, a calibration may be performed in a fluid of known viscosity, and then a subsequent measurement of diffusion can be used to determine the unknown viscosity of a fluid of interest.

In accordance with the present invention, inference of viscosity of a non-flowing liquid medium from an OCT measurement of diffusion made through a scattering membrane, such as a tympanic membrane, is taught for the first time. Such an inference was not previously possible, because it had not been recognized that the distribution of particle sizes might be characterized in a way that allows for effective inference of a viscosity. Moreover, the application of OCT to clinical evaluation of the middle ear through measurement of the viscosity of a middle ear effluent is also taught in accordance with the present invention.

While these measurements can also be made using low-coherence interferometry (non-scanning OCT), the combination of cross-sectional OCT images and DLS measurements of a MEE can be used to rapidly identify spatial non-uniformities across the tympanic membrane (TM) and MEE, compared to the single depth scans provided by LCI (non-scanning OCT).

Methods in accordance with the present invention apply OCT-based DLS measurements to observe MEEs in vivo and characterize their physical properties, and, among them, viscosity in particular. The description below describes a validation of methods of the present invention by estimating the S-E diffusion coefficient of suspensions of varying viscosities and particulate characteristics, as well as phantoms developed to mimic OM with MEE. Finally, this method is used to characterize several in vivo and ex vivo MEE samples from human subjects.

OCT-based ear imaging shows strong potential for clinical impact. In addition to the already established use of OCT for structural imaging and characterization of the middle ear, it is feasible using techniques in accordance with the present invention, to characterize the viscosity of MEEs non-invasively and in vivo. Eventually, this expanded set of information may be used to more accurately diagnose the wide spectrum of OM infection, and help physicians improve clinical decision making.

Optical Coherence Tomography System

A portable, handheld, OCT system, designated generally by numeral 100, is shown schematically in FIG. 1A. Such a system may be used to collect OCT data. OCT system 100 is preferably designed to be portable and easily transported to and from clinical sites.

In accordance with embodiments of the present invention, methods and apparatus are provided for deriving the viscosity of a fluid such as a middle ear effluent (MEE) by measuring scattering through a membrane adjacent to the fluid (such as an in vivo human TM) by using data acquired from OCT system 100, now described with reference to FIG. 1A. OCT system 100 may also be referred to herein, without loss of generality, as "hand-held OCT system" 100.

In one embodiment, hand-held imaging system 100, shown in FIG. 1A, includes a Fourier-domain OCT interferometer system 102 in which a reference arm 104 and a detection arm 106 of the OCT interferometer system 102 receive illumination from a broadband source 108 such as a superluminescent diode (SLD), available from Superlum of Cork, Ireland, centered at a wavelength of 860 nm, with a bandwidth of approximately 135 nm full width at half maximum (FWHM). OCT interferometer system 102 also includes a spectrometer unit 120, as available from Wasatch Photonics of Durham, N.C., with a spectral range of 940±40 nm and a line rate of up to 40 kHz, which includes a detector 122, typically, a linescan camera. Additional optical components include a 2×2 fiber coupler 130, with polarization paddles 132 on the reference 104 and sample 106 ports of the fiber coupler, and a free-space reference arm 134 with a mirror 136 for reflecting light back into the interferometer 134.

A hand-held probe 140 (the casing of which may be referred to herein as a "probe housing") houses sample arm 106 of the interferometer 134, typically along with optics for video otoscopic imaging. A probe nose-cone 142 is typical of those used in otoscopes, modified to include a focusing lens. White light is delivered from an LED (not shown) in the probe housing 140 to the sample via a fiber bundle (not shown) concentrically arranged at the distal end of the probe nose-cone 142. The optical path corresponding to video imaging (in the visible portion of the electromagnetic spectrum) is separated from the LCI imaging path (in the near-infrared portion of the electromagnetic spectrum) using a dichroic mirror 148.

Detector 122 generates a detector interference signal (entailing a cross-correlation of the scattered and reference fields) as a function of depth into a sampled fluid relative to a specified surface of the fluid. For example, the reference surface may be the tympanic membrane of the ear of a person, or other scattering membrane. The detector interference signal is cross-correlated by a cross-correlator 150, thereby deriving a mean cross-correlation function of at least one of amplitude, phase and intensity of a scattering signal for a plurality of depths into the fluid sample relative to the specified surface. The mean is taken over a transverse dimension at each depth. A processor 152 calculates a diffusion coefficient by fitting the mean cross-correlation function at each depth, and derives a viscosity characterizing the sampled fluid based on the diffusion coefficient, as described below.

Within the scope of the present invention, handheld probe 140 may utilize interchangeable tips to allow for both a wide field-of-view during benchtop imaging as well as compatibility with speculum tips used during human subject imaging. One example of an embodiment of the present invention, OCT system 100 is shown in FIG. 1B. The axial and transverse resolutions of the system are 2.4 μm and 15 μm, respectively, in air. Each cross-sectional image (B-scan) is 2048 pixels in depth, given by a line scan camera-based spectrometer 120, with 1000 adjacent columns (A-lines), collected at a frame rate of approximately 30 frames per second (FPS). Transverse beam scanning for acquiring B-scans is performed using a MEMS scanning unit (such as supplied by Advanced MEMS). To collect DLS data, a non-scanning (low-coherence interferometry) configuration may be used, with the beam incident on the sample. Additionally, a commercial USB video otoscope (such as supplied by Welch Allyn) may be used to collect high resolution surface images of the TM.

Inset 1C shows handheld probe 140 in a mounted configuration, used to measure phantom samples or aspirated ex vivo middle ear effusions, for example.

A prior art OCT otoscope 400 is shown schematically in FIG. 1D, which appears as FIG. 10 in the Boppart '934 patent. As described there, OCT otoscope 400 images the ear using optical coherence tomography, and includes a core imaging unit 410 in communication with a core software unit 430. Preferably, the core imaging unit 410 is not only in communication with, but also integrated within, OCT otoscope 400 so as to provide a compact portable instrument which allows straightforward clinical operation in an office-based setting. The core imaging unit 410 is in communication with the core software unit 430. If the core imaging unit 410 is integrated within OCT otoscope 400, then the core software unit can communicate directly with the d OCT otoscope 400.

In accordance with the operation of OCT devices, light emitted by a low-coherence source 402 is incident upon ear tissue via otoscope 401, and is combined with a reference beam, such as derived via reference mirror 424, in interferometer 408, thereby gating a detection signal to a tightly localized scattering window. The reference beam may share a common path with the signal beam and be reflected, for example, from a window in the signal beam path. Low-coherence source 402 may be swept in wavelength, and the interferometer output may be wavelength-resolved by spectrometer 412.

OCT otoscope 400 includes any imaging device which can non-invasively image the middle ear, direct and receive light from the middle ear and send the received light to the core imaging unit 410. Preferably, the OCT otoscope 400 also includes any device which can form a direct line of sight from the tympanic membrane to the outside of the ear, such as an ear speculum. The OCT otoscope 400 includes things such as an otoscope 401, a pneumatic otoscope. ear plugs, ear speculums, and other such devices. In one embodiment, the otoscope 401 is a pneumatic otoscope. such as the MacroView™ otoscope manufactured by Welch Allyn Inc. of Skaneateles Falls, N.Y., or the BETA 200 otoscope manufactured by HEINE Optotecltnik of Germany.

Preferably, the OCT otoscope 400 is adapted for selecting and analyzing tissue in the patient's middle ear. This means that the device is capable of non-invasively imaging inside the patient's ear canal and more specifically, non-invasively imaging the patient's middle ear. Preferably, at least a portion of the device is adapted for insertion into the patient's ear canal, allowing for non-invasive imaging of the patient's ear canal and or middle ear. In one embodiment, at least a portion of the OCT otoscope 400 has a diameter or width which does not exceed 1 cm and preferably does not exceed 0.5 cm, so that the OCT otoscope 400 can be inserted into an ear. However, since animal ears can be much larger than human ears, at least a portion of OCT otoscope 400 can be adapted for insertion into those ears and made much larger so as to fit within the ear canal of any animal, large or small. FIG. 2A shows an in vivo OCT image of a human tympanic membrane (TM) and Middle Ear Effusion (MEE), while inset FIG. 2B is a CCD image of the TM surface. FIG. 2C shows M-mode time-lapse data, single OCT A-scans taken repeatedly at the white dotted line (of FIG. 2A) through time.

Example: Measurement of MEE Phantoms

M-mode (repeated A-lines, acquired at a fixed transverse position over time) OCT data may obtained from the microparticle suspensions and MEE phantoms by fixing the probe in a mounted configuration, as shown in FIG. 1C. Before imaging, all samples are allowed to equilibrate to room temperature, approximately 25° C., thereby limiting the effects of turbulence that arises due to movement. In one example, twenty sequential M-mode images, each consisting of a total of 4,000 sequential A-lines (each A-line taken at a 31 μs exposure), were acquired from each of the samples.

Handheld probe 140 illuminates the TM with a 2.5 mW beam. Taking into account the dwell time needed for each of these non-scanning measurements (124 ms) and the central wavelength of 860 nm, this system provides a radiant exposure to the TM that is approximately 420 times lower than the ANSI (American National Standards Institute) Maximum Permissible Exposure (MPE) limit for skin. This optical exposure is further reduced during normal OCT imaging, as the beam rapidly sweeps over tissue at approximately 30 FPS, with far less single-point dwell time. This system, therefore, operates well below the ANSI MPE limit in either mode.

Example: Calibration—Microparticle Suspensions and Middle Ear Phantoms

To calculate an accurate value of the diffusion coefficient, particles undergoing Brownian motion at a known temperature and in a medium of known properties, including refractive index and viscosity, are needed. Therefore, to independently study the effect of particle size and viscosity on the S-E coefficient, two sets of three microparticle suspensions were created. For the first set, to vary the particle size, suspensions of non-functionalized polymer microbeads of three different average diameters, 0.54 μm, 1.14 μm, and 1.73 μm, were prepared by mixing the microparticles in distilled water. The second set was prepared by mixing 1.14 μm microbeads in three different water-glycerol mixtures (90/10, 70/30, 50/50, % volume glycol/% volume water), to obtain suspensions of varying viscosity. To ensure accurate mixing ratios, stock solutions of the water-glycerol mixtures were first created using a large diameter syringe to pipette glycerol, which was then diluted down to meet the specified mixture parameters. Microparticles were subsequently added to form the suspension and were thoroughly mixed with a standard touch vortex mixer for approximately two minutes.

Two types of phantoms were created to simulate the in vivo conditions of two infections by varying the viscosity of the MEE and the overall appearance and thickness of a simulated biofilm. The phantoms were created using two of the same microparticle suspensions described previously, using 1.14 μm microbeads and water-glycerol mixtures (90/10 and 50/50, % volume glycerol/% volume water). Thin plastic sheets, typically used in a head/ear training model for pneumatic otoscopy exams (available from Nasco), were used as a TM phantom, and petroleum jelly was used as a moderately scattering biofilm phantom. These phantoms are used to validate recovery the diffusion coefficient in a more complex, multi-structured sample.

Data Reduction

A traditional method of cumulants, is described, for example, by Frisken, *Appl. Opt.*, vol. 40, pp. 4087-91 (2001), which is incorporated herein by reference. The traditional method, or any variant thereof, may be employed for DLS data analysis, moreover any other method of data analysis is within the scope of the present invention. The method of cumulants is one of the most commonly used techniques for data analysis in DLS. In the method of cumulants, the intensity cross-correlation function of the scattered light is expressed in terms of a distribution of decay rates. Since this formulation takes into account the variability in the decay rate of the sample, and the fitting is performed around the mean utilizing the moments of the cross-correlation function, it is generally more robust to noise in the data.

FIGS. 3A-3C depict how a S-E diffusion coefficient is calculated for a sample, in accordance with an embodiment of the present invention. Starting with time-lapse axial depth scans (A-lines), a depth is selected and the intensity cross-correlation decay curve (Blue) is calculated, per FIG. 3B. The analytical expression for the second order intensity cross-correlation is fitted to the experimentally obtained temporal intensity cross-correlation data to estimate the diffusion coefficient D. M-mode OCT scale bar is approximately 200 μm in depth, where $\bar{g}^{(2)}(\tau)$ is the averaged temporal intensity-based cross-correlation function, D is the Stokes-Einstein diffusion constant and q is the scanning parameter as defined in the text.

First, in FIG. 3A, the raw spectral domain M-mode OCT data is resampled to be linear in wavenumber (k), and processed with a custom dispersion correction and Fast Fourier Transform (FFT) algorithm. Next, in FIG. 3B, the temporal intensity cross-correlation function is calculated for each depth over a user-specified depth range:

$$g^{(2)}(\tau) = \frac{\langle I(t) \rangle \langle I(t+\tau) \rangle}{\langle I(t) \rangle^2}$$

Then, in FIG. 3C, an average of the resulting cross-correlation functions is taken over repeated measurements to calculate a mean value for each depth. This helps to reduce the inherent statistical variation otherwise present. This data is then fit using the method of cumulants to estimate the parameter $\Gamma = Dq^2$. The parameter $\Gamma$, the decay rate, characterizes the rate of decay of the intensity cross-correlation function. The expression for $\Gamma$ contains both the (S-E) diffusion coefficient $$D = \frac{K_b T}{6\pi r \eta},$$

and q, where q is the scanning parameter, $$q = \frac{4\pi n \sin\left(\frac{\theta}{2}\right)}{\lambda},$$

and θ is defined as the scattering angle. These parameters are used to fit the data according to:

$$\bar{g}^{(2)}(\tau) = e^{-2Dq^2|\tau|}.$$

The intensity cross-correlation of a suspension of higher viscosity decays at a slower rate (i.e., a suspension of higher viscosity has smaller $\Gamma$) than a suspension of lower viscosity.

Assuming that the directly backscattered light from the sample (θ=180°) is collected with OCT, the $$\sin\left(\frac{\theta}{2}\right)$$

term becomes unity and the expression for the scanning parameter simplifies to $$q = \frac{4\pi n}{\lambda}.$$

Once q is known, an average value and standard deviation can be estimated for the diffusion coefficient D (in units of $cm^2/s$). If D is accurately estimated and if the particle size r is known, η can then be determined. In cases whether particle sizes vary substantially, as it does in middle ear effusions by more than two orders of magnitude, a measure of relative viscosity is obtained based on the decay rate of the cross-correlation function.

When imaging in vivo, data for analysis was collected from regions near the TM-MEE interface. This site selection helps to standardize data analysis between subjects by identifying a common feature, and helps reduce the contribution from multiple scattering effects that can alter the detected decay time.

Example: Clinical Human Subject Imaging

Human subjects were imaged in a surgical suite with a handheld OCT probe 140 (shown, e.g., in FIG. 1B). If present, effusions were first imaged in vivo immediately after the induction of anesthesia, but prior to myringotomy (incision in the TM) and tympanostomy tube placement. After myringotomy, the MEE was aspirated using a small metal cannula and vacuum line that fed to an exudate trap. The aspirated ex vivo MEEs were then observed and imaged in the trap using the handheld probe in the mounted configuration shown in FIG. 1C.

Example: Phantoms of Varying Particle Size and Viscosity

Figure 4A:
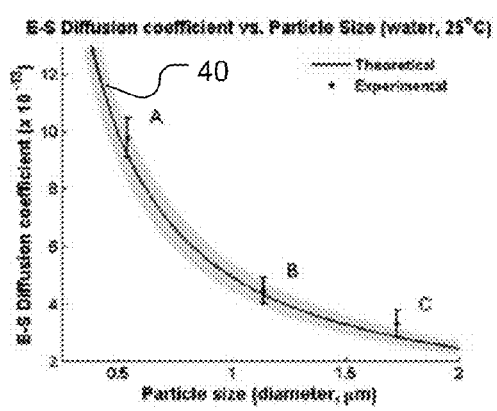
FIG. 4A plots experimentally determined Stokes-Einstein diffusion coefficients for microparticle solutions of varying particle sizes. Blue curve shows the theoretical trend, and Observed microparticles of increasing diameter (A=0.54 µm, B=1.14 µm, C=1.73 µm) suspended in water at room temperature.

Experimental calculation of particle size and viscosity of the suspensions using techniques in accordance with the present invention are now described with reference to FIGS. 4A-B. In FIG. 4A, a theoretical curve 40 displays the expected value based on the known properties of the samples: viscosity, room temperature, and particle diameter, with shaded area defining the approximate accuracy of the calculated theory, which is a function of microparticle manufacturing tolerances. The average and standard deviation of the experimentally obtained S-E diffusion coefficient data points are also show for each of four particle sizes, (A=0.54 μm, B=1.14 μm, C=1.73 μm, suspended in water at room temperature. The experimentally determined data closely match the expected theoretical values.

Figure 4B:
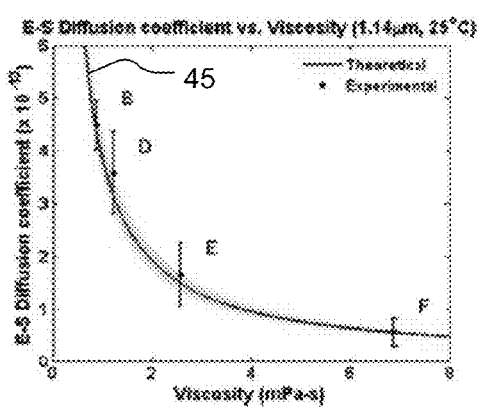
FIG. 4B plots experimentally determined Stokes-Einstein diffusion coefficients for microparticle solutions of varying viscosity.

FIG. 4B plots experimentally determined Stokes-Einstein diffusion coefficients for microparticle solutions of varying viscosity. Curve 45 shows the theoretical trend, and the adjoining shaded areas define the approximate accuracy of the calculated theory, which is a function of microparticle manufacturing tolerances. Observed 1.14 μm particles suspended in water and glycerol mixtures of varying increasing viscosity (B=100/0, D=90/10, E=70/30, F=50/50; % volume glycerol/% volume water) at room temperature are shown. Average and standard deviation of measured data are displayed (N=20). Note: Point B reflects the same data point as Point B in FIG. 4A.

In general, the agreement between the experimental and theoretical values depends on the accuracy of the known parameters of the S-E coefficient D, namely, the hydrodynamic particle size (r) and viscosity (η). In the presented experiments, the variance in the experimental estimates can be mainly attributed to the accuracy of the suspension preparation and volume mixing, as well as any variability in particle size diameter due to manufacturing tolerances, stated by the manufacturer to be near 5-10%. Shaded regions in both plots of FIGS. 4A and 4B reflect a 7% variance in size from the product specification, which provides reasonable limits on the accuracy of the particles' theoretically calculated behavior. Moreover, viscosity can change with temperature, although this is less of a concern in these well controlled samples.

Middle Ear Phantoms

To demonstrate non-invasive characterization of fluids through a scattering membrane, it is desirable to image through other interfaces or tissue, namely the TM and any potential biofilm-related structures that may be affixed to the TM. Methods in accordance with the invention have the benefit of depth-resolved measurements by using OCT, as detailed in FIGS. 5A-5B. Four marked depth ranges, 51, 52, 53 and 54 were processed through an algorithm in accordance with the present invention, showing no appreciable signals from the static non-moving portions of the phantom, namely, air 51 within the ear canal, TM tissue 52, or the thick adherent biofilm phantom 53. FIG. 5B demonstrates that any meaningful signals, namely curve 514, derives only from the effusion, and not from other fixed structures or potential sources of error or noise which give rise to generally flat plots 513 that show no cross-correlation with time. Stokes-Einstein diffusion coefficient measurements of middle ear phantoms, with calculated S-E diffusion coefficients, are plotted in FIG. 6B for phantoms imaged in FIG. 6A. The phantoms (A, B) each contain a different effusion-like suspension (suspension of water, glycerol, and micro-particle mixtures) to mimic the physiological qualities of a 'serous' and 'mucoid' middle ear effusion. Scale bars 60 represent 100 µm in depth.

Subsequently, a method in accordance with the present invention was demonstrated on MEE phantoms (FIGS. 8 and 9) based on phantom samples D and F from FIG. 5, which were selected to more closely mimic the biomechanical properties of MEEs. This phantom served as a final proof-of-concept measurement using water- and glycerol-based samples observed through a more realistic phantom with simulated TM and biofilm. The cross-sectional OCT images of the phantoms shown in FIGS. 8A and 8B clearly show the additional biofilm-like structure and the scattering effusion-like features. The experimental S-E coefficient of each phantom was determined and found to match the theoretical value of the MEE phantom, as shown in FIG. 9. It is important to note that by looking solely at the static OCT images, no obvious determination can be made to differentiate these samples. A prior study of roughly 100 subjects used a commercial magnetic rheometer to observe MEE samples and showed a measurable difference in human MEE viscosity between serous and mucoid effusion types. The findings of this previous study, along with the analysis of MEE phantoms presented here, lends credibility that this technique can effectively analyze different types of MEE samples.

Analysis of In Vivo and Ex Vivo Clinical Data

Efficacy of methods applied to human MEEs in a clinical setting is now discussed with reference to FIGS. 7 and 8. The characteristic dimensions of particles suspended within MEEs are known to range over greater than two orders of magnitude.

Figure 7C:
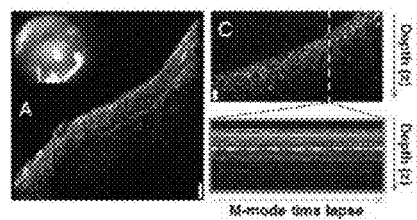
FIG. 7A shows an in vivo cross-sectional OCT image with an inset high-resolution otoscope image 701 from a patient with an effusion, while FIG. 7D show an effusion from another patient.
FIGS. 7B and 7E show cross-sectional images of the respective aspirated ex vivo MEEs in an exudate trap, with the subsequently measured time-lapse M-mode OCT data shown in FIGS. 7C and 7F. The plot in FIG. 7G shows the comparison of the normalized second order correlation plots of the aspirated ex vivo MEEs.
Figure 7G:
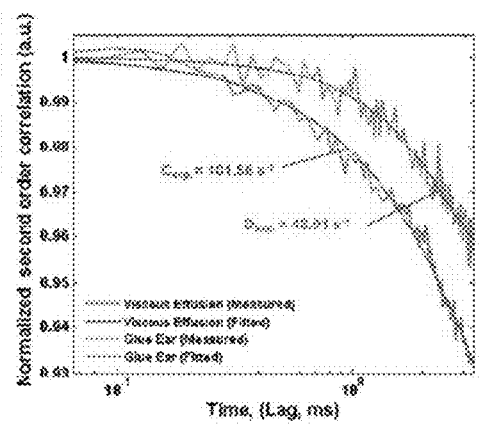
Figure 7F:
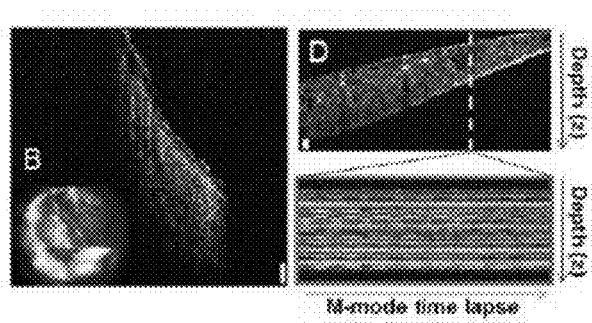

FIGS. 7A-7G and 8A-8E show the comparison of a MEE observed in vivo and then ex vivo after aspiration. FIG. 7 shows the comparison between two separate MEE samples. FIG. 7A shows an in vivo cross-sectional OCT image with an inset high-resolution otoscope image from a patient with an effusion, while FIG. 7D show an effusion from another patient. FIGS. 7B and 7E show cross-sectional images of the respective aspirated ex vivo MEEs in an exudate trap, with the subsequently measured time-lapse M-mode OCT data shown in FIGS. 7C and 7F. The plot in FIG. 7G shows the comparison of the normalized second order correlation plots of the aspirated ex vivo MEEs, where the data from FIGS. 7A-7C has a decay constant of 101.58 s$^{-1}$, while the data from FIGS. 7D-7F has a value of 48.01 s$^{-1}$. These quantitative results suggest that the effusion from the subject shown in FIG. 7D has a more viscous effusion (higher relative viscosity) than the subject in FIG. 7A, which is in agreement with the qualitative clinical assessment.

FIGS. 8A-8E the comparison between two separate MEE samples. FIG. 8A shows an in vivo cross-sectional OCT image and inset high-resolution otoscope image 801 from a patient with a thick effusion, while FIG. 8C shows an effusion from another patient. FIGS. 8B and 8D show cross-sectional images of the respective aspirated ex vivo MEEs in an exudate trap, with the subsequently measured time-lapse M-mode OCT data. The plot in FIG. 8E shows the comparison of the normalized second order correlation plots of the aspirated ex vivo MEEs, where the data from FIG. 8A has a decay constant of 101.58 s$^{-1}$, while the data from FIG. 8B has a value of 48.01 s$^{-1}$. These quantitative results suggest that the effusion from the subject shown in FIG. 8B has a more viscous effusion (higher relative viscosity) than the subject in FIG. 8A, which is in agreement with the qualitative clinical assessment.

Discrepancies in measurements between in vivo and aspirated effluent can be partly explained by the differences in the imaging conditions of the two samples—within the middle ear and after aspiration within the exudate trap. These sample conditions will differ mainly in structure and temperature. The aspiration process will disturb the biofilm structure affixed to the TM and rapidly cool the total contents of the MEE, including any fluid and bacterial components, from body temperature to operating room temperature (from approximately 37° C. to 22° C. as measured with an in-room thermometer). As in most fluids or colloids, a drop in temperature will cause an increase in viscosity, which most likely caused the lengthening of the decay time in the ex vivo MEE sample with respect to the in vivo MEE sample.

While typical DLS analyses assume that the particles undergoing undisturbed Brownian motion are spherical in shape and are suspended in a uniformly viscous solution, MEEs can be complex, perhaps aggregated, mixtures of different sized and likely non-spherical particles (e.g. immune cells, blood cells, and bacteria), varying in size by more than two orders of magnitude. This problem was partially mitigated by employing the cumulants method for analyzing the data, which takes into account the possible polydisperse nature of the MEE. Methods in accordance with the present invention may advantageously quantify and grade different types of chronic viscous and mucopurulent effusions, and do so in vivo.

In accordance with certain embodiments of the present invention, aspects of the measurement of the viscosity of a fluid, described herein, may be implemented as a computer program product for use with a computer system. Such implementations may include a series of computer instructions fixed either on a tangible medium, which is preferably non-transient and substantially immutable, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Related teachings may be found in Monroy et al., "*Noninvasive optical assessment of viscosity of middle ear effusions in otitis media,*" *J. Biophotonics*, DOI: 10.1002/jbio.201500313 2016. (2016), incorporated herein by reference.

The embodiments of the invention described above are intended to be merely exemplary; numerous variations and modifications will be apparent to those skilled in the art. All such variations and modifications are intended to be within the scope of the present invention as defined in any appended claims.

We claim:
1. A method for ascertaining a relative viscosity characterizing a fluid sample, the method comprising:
 a. illuminating the fluid sample through a scattering membrane adjacent to the fluid with broadband radiation having a fraction bandwidth, at half-maximum, of at least 10%;
 b. detecting scattering from scattering particles within the fluid sample, the scattering particles characterized by a distribution of characteristic dimensions spanning at least two orders of magnitude;
 c. generating a wavelength-resolved detector signal for deriving coherent scatter as a function of depth relative to a specified surface of the scattering membrane at a plurality of temporal delays;
 d. interferometrically deriving at least one of amplitude, phase and intensity of a scattered optical field for a plurality of depths relative to the specified surface;
 e. calculating a mean cross-correlation function for each depth;
 f. fitting the mean cross-correlation function for the plurality of depths to obtain a diffusion coefficient; and
 g. deriving the relative viscosity characterizing the fluid based on the diffusion coefficient.

2. A method in accordance with claim 1, wherein illuminating the fluid sample through a scattering membrane adjacent to the fluid sample includes transmitting the broadband radiation through an intervening biological membrane.

3. A method in accordance with claim 2, wherein the intervening biological tissue is a tympanic membrane.

4. A method in accordance with claim 1, wherein the fluid sample is a middle ear effusion.

5. A method in accordance with claim 1, further comprising calibrating a cross-correlation function decay rate relative to viscosity on the basis of a reference fluid of known viscosity.

6. A method in accordance with claim 4, further comprising grading the middle ear effusion with respect to at least one of serosity and mucosity.

* * * * *